United States Patent
Fujimoto (10) Patent No.: US 6,912,907 B2
(45) Date of Patent: Jul. 5, 2005

(54) ULTRASONIC APPARATUS AND METHOD FOR MEASURING THE CONCENTRATION AND FLOW RATE OF GAS

(75) Inventor: Naotoshi Fujimoto, Hino (JP)

(73) Assignee: Teijin Limited, Osaka (JP)

(*) Notice: Subject to any disclaimer, the term of this patent is extended or adjusted under 35 U.S.C. 154(b) by 0 days.

(21) Appl. No.: 10/239,227

(22) PCT Filed: Jan. 22, 2002

(86) PCT No.: PCT/JP02/00438

§ 371 (c)(1),
(2), (4) Date: Sep. 20, 2002

(87) PCT Pub. No.: WO02/057770

PCT Pub. Date: Jul. 25, 2002

(65) Prior Publication Data

US 2003/0136193 A1 Jul. 24, 2003

(30) Foreign Application Priority Data

Jan. 20, 2001 (JP) .......................... 2001-12861
Jan. 22, 2001 (JP) .......................... 2001-12862

(51) Int. Cl.⁷ .............................................. G01F 1/66
(52) U.S. Cl. ................... 73/597; 73/861.27; 73/861.28; 73/1.16
(58) Field of Search ............................ 73/597, 861.27, 73/861.28, 861.29, 24.01, 24.06, 1.06, 1.16

(56) References Cited

U.S. PATENT DOCUMENTS

| | | | | |
|---|---|---|---|---|
| 4,397,194 A | * | 8/1983 | Soltz ........................ | 73/861.28 |
| 4,483,202 A | * | 11/1984 | Ogura et al. .............. | 73/861.27 |
| 5,247,826 A | | 9/1993 | Frola et al. | |
| 5,501,098 A | * | 3/1996 | Cadet et al. .................. | 73/597 |
| 5,557,047 A | * | 9/1996 | Koide ......................... | 73/597 |
| 5,627,323 A | * | 5/1997 | Stern ........................ | 73/861.28 |
| 5,770,806 A | * | 6/1998 | Hiismaki ................. | 73/861.29 |
| 6,308,572 B1 | * | 10/2001 | Ishikawa et al. .............. | 73/597 |
| 6,435,038 B1 | * | 8/2002 | Nam ....................... | 73/861.27 |
| 6,532,828 B1 | * | 3/2003 | Delsing ................... | 73/861.29 |

FOREIGN PATENT DOCUMENTS

| | | | | |
|---|---|---|---|---|
| JP | 4-353751 | 12/1992 | | |
| JP | 6-213877 | 8/1994 | | |
| JP | 6-235721 | 8/1994 | | |
| JP | 7-209265 | 8/1995 | | |
| JP | 07209265 A | * | 8/1995 | .......... G01N/29/18 |
| JP | 8-233718 A | 9/1996 | | |
| JP | 2000-206133 | 7/2000 | | |

* cited by examiner

*Primary Examiner*—Hezron Williams
*Assistant Examiner*—Nashmiya Fayyaz
(74) *Attorney, Agent, or Firm*—Rader, Fishman & Grauer PLLC (57) ABSTRACT

An apparatus for measuring a gas concentration comprises a conduit through which an objective gas to be measured flows, a ultrasonic transmitting and receiving element fixed in a straight portion of the conduit and a reflecting plate fixed in the straight portion to face to the ultrasonic transmitting and receiving element. The apparatus further comprises a calibration gas source for supplying a calibration gas of which components and component ratio are preliminarily known, temperature sensors for measuring the temperature of the calibration gas flowing through the conduit, a propagation time calculating means for calculating the time period for propagation of the ultrasonic through the calibration gas in the conduit, a calibration means for calibrating the reference distance between the ultrasonic transmitting and receiving element and the reflecting plate based on the calculation results of the propagation time calculating means.

8 Claims, 2 Drawing Sheets

ULTRASONIC APPARATUS AND METHOD FOR MEASURING THE CONCENTRATION AND FLOW RATE OF GAS

TECHNICAL FIELD

The invention relates to ultrasonic apparatus and method for measuring the concentration of oxygen gas in a sample gas and flow rate of the sample gas, which is supplied from an oxygen concentrator used for a medical purpose.

BACKGROUND ART

It is well known that the propagation velocity of ultrasonic waves through a sample gas is presented by a function of the concentration and the temperature of the sample gas. The velocity of ultrasonic waves C(m/sec) propagating through a sample gas is presented by following equation (1) with mean molecular weight M and the temperature T(K).

$$C=(\kappa RT/M)^{1/2} \quad (1)$$

Where;
$\kappa$: ratio of molecular specific heat at constant volume and molecular specific heat at constant pressure
R: universal gas constant Therefore measuring the velocity of ultrasonic waves C(m/sec) propagating through a sample gas and the temperature T(K) of the sample gas will provide the mean molecular weight M of the sample gas through a calculation. For example, the mean molecular weight M of a sample gas containing an oxygen-nitrogen gas mixture of a mixture ratio P:(1−P) ($0 \leq P \leq 1$) will be calculated by $M=M_{O2}P+M_{N2}(1-P)$, where $M_{O2}$: Molecular Weight of oxygen and $M_{N2}$: Molecular Weight of nitrogen. Therefore, the oxygen concentration P will be obtained through a calculation on the basis of the measurement of mean molecular weight M. When the sample gas is an oxygen-nitrogen mixture, $\kappa=1.4$ is reasonable over a wide range of the oxygen-nitrogen mixture ratio.

When the velocity of ultrasonic waves propagating through a sample gas is C(m/sec) and the flow velocity of the sample gas is V(m/sec), the velocity of ultrasonic waves $V_1$(m/sec) propagating in the forward direction relative to the sample gas flow is $V_1=C+V$, and the velocity of ultrasonic waves $V_2$(m/sec) propagating in the backward direction relative to the sample gas flow is $V_2=C+V$. Therefore, the velocity of the sample gas flow V(m/sec) is calculated by following equation (2).

$$V=(V_1-V_2)/2 \quad (2)$$

The flow rate (m³/sec) of the sample gas will be obtained by multiplying this by the sectional area (m²) of the conduit through which the sample gas flows.

Methods and apparatuses for measuring the concentration of a certain gas or the flow velocity of a sample gas, by using the above principle, on the basis of the propagation velocity or the propagation time of ultrasonic waves through the sample gas have been developed. For example, Japanese Unexamined Patent Publication (Kokai) No. 6-213877 describes an apparatus for measuring the concentration and the flow rate of a sample gas by measuring the propagation time of ultrasonic waves propagating between two ultrasonic transducers opposingly disposed in a conduit through which the sample gas flows. Further, Japanese Unexamined Patent Publications (Kokai) No. 7-209265 and No. 8-233718 describe an apparatus for measuring the concentration of a certain gas contained in a sample gas by measuring the propagation velocity or propagation time of ultrasonic waves propagating through a volume with a reflecting type apparatus including a ultrasonic transducer and an opposingly disposed reflector.

In such a method and an apparatus for measuring the concentration and the flow rate by using the propagation velocity of the ultrasonic waves, it is necessary to accurately determine the propagation length of the ultrasonic waves, that is the distance between the transducers or between the transducer and the reflector, and the inner diameter of the conduit. However, the propagation length and the inner diameter of a conduit are adversely affected by the changes in the size of the conduit due to the changes in the temperature of the sample gas. Further, the propagation length of ultrasonic waves and the inner diameter of a conduit are also affected by the accuracies in machining or assembling the conduit, assembling the ultrasonic transducer and the reflector, and machining the ultrasonic transducer. Therefore, it is difficult to obtain the propagation length of ultrasonic waves and the inner diameter of a conduit accurately, which reduces the measurement accuracy.

Above described Japanese Unexamined Patent Publications (Kokai) No. 6-213877 and No. 8-233718 describe a temperature correction factor introduced to improve the temperature characteristics of the concentration measurement results. Further, there is a method in which the relations between the temperature, the propagation velocity of ultrasonic waves and the concentration are stored in a memory device as a table. However, in order to obtain such a temperature correction factor or table, a sample gas must be supplied to the device at various different temperatures to previously obtain the temperature characteristics of the apparatus. Therefore, a large amount of effort is required.

Further, a method for minimizing the temperature characteristics of the measurement results has been proposed in which whole of an apparatus is disposed under a temperature control for the measurement at a constant temperature. However, in this method, there is a problem that it is difficult to accurately control the temperature of the apparatus, in particular the conduit in addition to the necessity of a separate facility for conducting the temperature control.

DISCLOSURE OF THE INVENTION

The objective of the present invention is to provide a ultrasonic concentration measuring apparatus and method which allows the calibration of the apparatus by a simple method and can accurately measure the concentration of a certain gas in a sample gas independently of the temperature of the sample gas.

Further, the objective of the present invention is to provide a ultrasonic flow rate measuring apparatus and method which allows the calibration of the apparatus by a simple method and can accurately measure the flow rate of a sample gas independently of the temperature of the sample gas.

According to the present invention, there is provided a ultrasonic apparatus for measuring a gas concentration, comprising: a conduit for flowing an objective gas, the concentration of which is to be measured; a ultrasonic transmission-reception device mounted to the inside of the conduit; a reflector mounted to the inside of the conduit to face the ultrasonic transmission-reception device; a transmission-reception switch for switching the operation mode of the ultrasonic transmission-reception device between a transmission mode for transmitting ultrasonic waves and a reception mode for receiving ultrasonic waves; a calibration gas source for supplying a calibration gas, the component and the component ratio of which are known, to the conduit;

a temperature sensor, disposed in the conduit, for measuring the temperature of the calibration gas flowing through the conduit; propagation time calculation means for calculating the time period where the ultrasonic waves propagates through the calibration gas in the conduit on the basis of the time when the ultrasonic transmission-reception device transmits the ultrasonic waves and the time when the ultrasonic transmission-reception device receives the ultrasonic waves reflected by the reflector; and calibration means for calibrating a reference length between the ultrasonic transmission-reception device and the reflector on the basis of the calculation results by the propagation time calculation means.

Further, according to another feature of the invention, there is provided a method of measuring the concentration of an objective gas by a ultrasonic gas concentration measuring apparatus which comprises, a conduit for flowing an objective gas, the concentration of which is to be measured, a ultrasonic transmission-reception device mounted to the inside of the conduit, a reflector mounted to the inside of the conduit to face the ultrasonic transmission-reception device, and a transmission-reception switch for switching the operation mode of the ultrasonic transmission-reception device between a transmission mode for transmitting ultrasonic waves and a reception mode for receiving ultrasonic waves; the method comprising, prior to the start of the process for measuring the concentration of the gas to be measured, the steps of: supplying a calibration gas, the component and the component ratio of which are known, to the conduit; measuring the temperature of the calibration gas flowing through the conduit by a temperature sensor disposed in the conduit; generating ultrasonic waves by the ultrasonic transmission-reception device; switching the operation mode of the transmission-reception device from the transmission mode for transmitting the ultrasonic waves to the reception mode for receiving the ultrasonic waves; calculating propagation time period where the ultrasonic waves propagates through the calibration gas in the conduit on the basis of the time when the ultrasonic transmission-reception device transmits the ultrasonic waves and the time when the ultrasonic transmission-reception device receives the ultrasonic waves reflected by the reflector; and calibrating a reference length between the ultrasonic transmission-reception device and the reflector on the basis of the calculation results.

Further, according to another feature of the invention, there is provided a ultrasonic apparatus for measuring a gas concentration, comprising: a conduit for flowing an objective gas, the concentration of which is to be measured; a first ultrasonic transmission-reception device mounted to the inside of the conduit; a second ultrasonic transmission-reception device mounted to the inside of the conduit to face the first ultrasonic transmission-reception device; a transmission-reception switch for switching the operation mode of the first and second ultrasonic transmission-reception devices between a transmission mode for transmitting ultrasonic waves and a reception mode for receiving ultrasonic waves; a calibration gas source for supplying a calibration gas, the component and the component ratio of which are known, to the conduit; a temperature sensor, disposed in the conduit, for measuring the temperature of the calibration gas flowing through the conduit; propagation time calculation means for calculating a first propagation time period where the ultrasonic waves propagates through the calibration gas in the conduit on the basis of the time when the first ultrasonic transmission-reception device transmits the ultrasonic waves and the time when the second ultrasonic transmission-reception device receives the ultrasonic waves, and a second propagation time period where the ultrasonic waves propagates through the calibration gas in the conduit on the basis of the time when the second ultrasonic transmission-reception device transmits the ultrasonic waves and the time when the first ultrasonic transmission-reception device receives the ultrasonic waves; and calibration means for calibrating a reference length between the first and second ultrasonic transmission-reception devices on the basis of the calculation results by the propagation time calculation means.

Further, according to another feature of the invention, there is provided a method of measuring the concentration of an objective gas by a ultrasonic gas concentration measuring apparatus which comprises, a conduit for flowing an objective gas, the concentration of which is to be measured, a first ultrasonic transmission-reception device mounted to the inside of the conduit, a second ultrasonic transmission-reception device mounted to the inside of the conduit to face the first ultrasonic transmission-reception device, and a transmission-reception switch for switching the operation mode of the first and second ultrasonic transmission-reception devices between a transmission mode for transmitting ultrasonic waves and a reception mode for receiving ultrasonic waves; the method comprising, prior to the start of the process for measuring the concentration of the gas to be measured, the steps of: supplying a calibration gas, the component and the component ratio of which are known, to the conduit; measuring the temperature of the calibration gas flowing through the conduit by a temperature sensor disposed in the conduit; generating ultrasonic waves by the first ultrasonic transmission-reception device and receiving the ultrasonic waves by the second ultrasonic transmission-reception device; switching the operation mode of the first transmission-reception device from the transmission mode to the reception mode and the operation mode of the second transmission-reception device from the reception mode to the transmission mode; calculating a first propagation time period where the ultrasonic waves propagates through the calibration gas in the conduit on the basis of the time when the first ultrasonic transmission-reception device transmits the ultrasonic waves and the time when the second ultrasonic transmission-reception device receives the ultrasonic waves, and a second propagation time period where the ultrasonic waves propagates through the calibration gas in the conduit on the basis of the time when the second ultrasonic transmission-reception device transmits the ultrasonic waves and the time when the first ultrasonic transmission-reception device receives the ultrasonic waves; and calibrating a reference length between the first and second ultrasonic transmission-reception devices on the basis of the calculation results.

Further, according to another feature of the invention, there is provided a ultrasonic apparatus for measuring a gas flow rate, comprising: a conduit for flowing an objective gas, the concentration of which is to be measured; a first ultrasonic transmission-reception device mounted to the inside of the conduit; a second ultrasonic transmission-reception device mounted to the inside of the conduit to face the first ultrasonic transmission-reception device; a transmission-reception switch for switching the operation mode of the first and second ultrasonic transmission-reception devices between a transmission mode for transmitting ultrasonic waves and a reception mode for receiving ultrasonic waves; a calibration gas source for supplying a calibration gas, the component and the component ratio of which are known, to the conduit; a temperature sensor, disposed in the conduit, for measuring the temperature of the calibration gas flowing through the conduit; propagation time calculation means for calculating a first propagation time period where the ultrasonic waves propagates through the calibration gas in the conduit on the basis of the time when the first ultrasonic transmission-reception device transmits the ultrasonic waves and the time when the second ultrasonic transmission-reception device receives the ultrasonic waves, and a second propagation time period where the ultrasonic waves propagates through the calibration gas in the conduit on the basis of the time when the second ultrasonic transmission-reception device transmits the ultrasonic waves and the time when the first ultrasonic transmission-reception device receives the ultrasonic waves; and calibration means for calibrating a reference length between the first and second ultrasonic transmission-reception devices and the inner diameter of the conduit, on the basis of the calculation results by the propagation time calculation means.

Further, according to another feature of the invention, there is provided a method of measuring the flow rate of an objective gas by a ultrasonic gas concentration measuring apparatus which comprises, a conduit for flowing an objective gas, the concentration of which is to be measured, a first ultrasonic transmission-reception device mounted to the inside of the conduit, a second ultrasonic transmission-reception device mounted to the inside of the conduit to face the first ultrasonic transmission-reception device, and a transmission-reception switch for switching the operation mode of the first and second ultrasonic transmission-reception devices between a transmission mode for transmitting ultrasonic waves and a reception mode for receiving ultrasonic waves; the method comprising, prior to the start of the process for measuring the concentration of the gas to be measured, the steps of: supplying a calibration gas, the component and the component ratio of which are known, to the conduit; measuring the temperature of the calibration gas flowing through the conduit by a temperature sensor disposed in the conduit; generating ultrasonic waves by the first ultrasonic transmission-reception device and receiving the ultrasonic waves by the second ultrasonic transmission-reception device; switching the operation mode of the first transmission-reception device from the transmission mode to the reception mode and the operation mode of the second transmission-reception device from the reception mode to the transmission mode; calculating a first propagation time period where the ultrasonic waves propagates through the calibration gas in the conduit on the basis of the time when the first ultrasonic transmission-reception device transmits the ultrasonic waves and the time when the second ultrasonic transmission-reception device receives the ultrasonic waves, and a second propagation time period where the ultrasonic waves propagates through the calibration gas in the conduit on the basis of the time when the second ultrasonic transmission-reception device transmits the ultrasonic waves and the time when the first ultrasonic transmission-reception device receives the ultrasonic waves; and calibrating a reference length between the first and second ultrasonic transmission-reception devices and the inner diameter of the conduit, on the basis of the calculation results.

BEST MODE FOR CARRYING OUT THE INVENTION

A preferred embodiment of the present invention will be described below. In the embodiment described below, a case is indicated as an example in which the sample gas is composed of a mixture of oxygen and nitrogen. However, the measurable sample gas is not limited to a sample gas of oxygen and nitrogen and the present invention can be supplied to a mixture including another gases.

Figure 1:
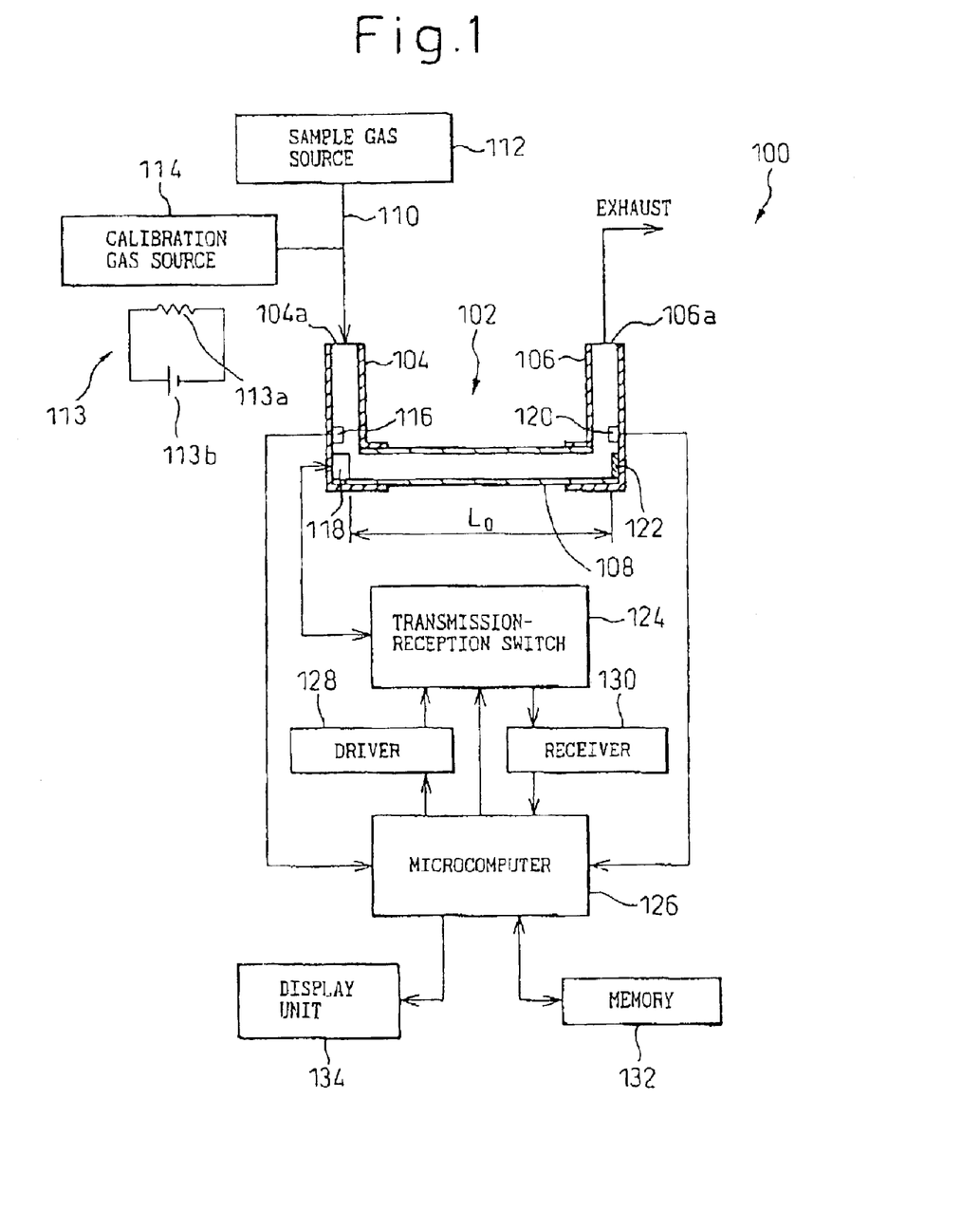
FIG. 1 is a schematic diagram of an apparatus according to a first embodiment of the invention.

FIG. 1 shows a schematic diagram of a ultrasonic gas concentration measuring apparatus according to a first embodiment of the present invention. The apparatus 100 includes a conduit 102 for flowing a sample gas or a calibration gas. The conduit 102 has a straight portion 108 and perpendicular portions 104 and 106 connected to the ends of the straight portion. A ultrasonic transducer 118 is fixedly provided at an end of the inside of the straight portion 108 as a ultrasonic transmission-reception device, and a reflector 122 is fixedly mounted to the other end of the inside of the straight portion 108 to face the ultrasonic transducer 118. In this embodiment, the distance between the ultrasonic transducer 118 and the reflector 122 is defined as a test length.

A transmission-reception switch 124 is connected to the ultrasonic transducer 118. The transmission-reception switch 124 switches the operation mode of the ultrasonic transducer 118 between a transmission mode in which the ultrasonic transducer 118 transmits ultrasonic waves and a reception mode in which the ultrasonic transducer 118 receives the ultrasonic waves. The transmission-reception switch 124 is connected to a microcomputer 126 so that the switching operation of transmission-reception switch 124 is controlled by the microcomputer 126.

The perpendicular portion 104, disposed at the upstream side relative to the flow direction of the gas through the conduit 102, has an inlet port 104a. A sample gas source 112 and a calibration gas source 114 are connected to the inlet port 104a through a supply conduit 110. The sample gas source 112 includes a vessel (not shown) for containing a sample gas or a mixture including a gas, the concentration of which is to be measure and a pressure reducing valve (not shown) provided between the vessel and the supply conduit 110.

The calibration gas source 114 may include a vessel (not shown) for containing a calibration gas, the component and the component ratio of which is known, for example, a gas mixture including 20% of oxygen and 80% of nitrogen, and a pressure reducing valve (not shown) provided between the vessel and the supply conduit 110. The calibration gas source 114 may also include a temperature regulator 113, which provide means for changing the temperature of the device 100, in particular the conduit 102. In the example shown in FIG. 1, the temperature regulator 113 includes a heating wire 113a and an electric power source 113b for supplying the electric power to the heating wire 113a.

The perpendicular portion 106, disposed at the downstream side relative to the flow direction of the gas through the conduit 102, has an outlet port 106a. The sample gas or the calibration gas used for the concentration measurement or the calibration is exhausted through the outlet port 106a. A gas processing apparatus (not shown) may advantageously be disposed downstream of the outlet port 106 in case that the exhausted gas is not suitable to directly exhaust to the atmosphere.

Temperature sensors 116 and 120, for measuring the temperature of the sample gas or the calibration gas flowing through the conduit 102, are disposed preferably in the perpendicular portions 104 and 106 so that they do not disturb the flow in the straight portion 108. The temperature sensors 116 and 120 are connected to the microcomputer 126. In this connection, if the changes in the temperature of the sample gas is small, only one of the temperature sensors 116 or 120 may be disposed.

A driver 128 for driving the ultrasonic transducer 118, a receiver 130 for A/D conversion of the signals from the ultrasonic transducer 118, a display unit 134 for indicating, for example, the operating condition of the device 100 and the measurement results and memory 133 including a non-volatile memory device or a disc device for storing the operation system for the microcomputer 126 and various parameters are connected to the microcomputer 126

The operation of the first embodiment will be described below.

First, prior to the initiation of the normal measuring process for measuring the concentration of a certain gas contained in the sample gas, the test length between the ultrasonic transmission-reception device 118 and the reflector 122 is calibrated, in accordance with the sequence described below, to obtain the reference length $L_0$.

A gas mixture, the component and the component ratio of which are known, for example an oxygen-nitrogen gas mixture of which mixture ratio is P:(1−P) (0≦P≦1), is supplied to the conduit 102 as the calibration gas. At that time, the temperatures of the calibration gas are measured by the two temperature sensors 116 and 120 and the mean value thereof is stored in the memory 132 as a reference temperature $T_0(K)$. The reference temperature $T_0(K)$ may be any value which does not exceed the working temperature range of the device.

During the supply of the calibration gas, pulses for generating the ultrasonic waves are transmitted to the driver 128 from the microcomputer 126. A pulse voltage is supplied to the ultrasonic transducer 118 from the driver 128 through the transmission-reception switch 124. The ultrasonic transducer 118 generates ultrasonic waves corresponding to the pulse voltage. The ultrasonic waves generated by the ultrasonic transducer 118 propagate through the sample gas flowing through the straight portion 108 of the conduit 102 and are reflected by the reflector 122 to return to the ultrasonic transducer 118. In order to enable the ultrasonic transducer 118 to receive the returned ultrasonic waves, the transmission-reception switch 124 switches the operation mode of the ultrasonic transducer from the transmission mode to the reception mode right after the application of the pulse voltage to the ultrasonic transducer 118. The ultrasonic transducer 118 generates an electric signal corresponding to the received ultrasonic waves to the microcomputer 126 through the transmission-reception switch 124 and the receiver 130. The microcomputer 126 calculates the propagation time $t_0(sec)$ on the basis of the time when the transmitted pulses are generated to the first transducer 118 and the time when the electric signal is received from the ultrasonic transducer 118.

In this connection, the ultrasonic propagation velocity $C_0(m/sec)$ through the calibration gas at a temperature $T_0(K)$ is calculated by the equation (3) on the basis of above-described equation (1).

$$C_0=((\kappa R T_0)/(M_{O2}P+M_{N2}(1-P)))^{1/2} \quad (3)$$

On the other hand, the relation $$C_0=2L_0/t_0 \quad (4)$$

gives the following equation.

$$L_0=((\kappa R T_0)/(M_{O2}P+M_{N2}(1-P)))^{1/2} \times t_0/2 \quad (5)$$

Further, in the first embodiment, if the ultrasonic propagation velocity through a static calibration gas is C(m/sec) and the flow velocity of the sample gas from the ultrasonic transducer 118 toward the reflector 122 is V(m/sec), then the ultrasonic propagation velocity from the ultrasonic transducer 118 to the reflector 122 is C+V and the ultrasonic propagation velocity in the direction of the ultrasonic waves reflected to the ultrasonic transducer 118 by the reflector 122 is C−V. Accordingly, the ultrasonic propagation velocity measured by the apparatus 100 of the first embodiment is the mean velocity of the reciprocating ultrasonic waves. Therefore, the flow velocity V of the sample gas is cancelled to allow the ultrasonic propagation velocity C through the static sample gas.

These calculations are conducted by the microcomputer 126. The test length $L_0(m)$ thus calculated at the reference temperature $T_0$ is stored in the memory 132 as the reference length.

The reference length $L_0(m)$ between the ultrasonic transducer 118 and the reflector 122 at the temperature $T_0(K)$ is calibrated according the above method by supplying a calibration gas, the component and the component ratio of which is known, to the device 100 and measuring the propagation time $t_0(sec)$ of the ultrasonic waves generated by the ultrasonic transducer 118. This calibration process can be automatically completed by the microcomputer 126 through a simple operation, for example one push of a button (not shown) provided on the device 100 when the calibration gas is supplied. Further, the process can be completed on the instant because the calculation itself is simple. Further, if the relative position between the ultrasonic transducer 118 and the reflector 122 is changed due to the secular change in the device 100, the device can be easily calibrated again to renew the reference temperature and the reference length stored in the memory 132.

A method of measuring the oxygen concentration in a sample gas containing unknown concentrations of oxygen and nitrogen will be described below.

First, the explanation will be directed to an example in which the linear expansion coefficient $\alpha(1/K)$ of the conduit 102 is known.

When a measurement of a sample gas is conducted, the test length $L_S(m)$ at a temperature $T_S(K)$ can be obtained by reading the reference length $L_0(m)$ and the reference temperature $T_0(K)$ which have been stored in the memory 132 and by correcting the reference length $L_0(m)$ according to the following equation (6). The measured temperature $T_S(K)$ can be the mean value of temperatures sensed by the temperature sensors 116 and 120.

$$L_S=L_0(1+\alpha(T_S-T_0)) \quad (6)$$

The ultrasonic transducer 118 is set to the transmission mode when a sample gas is supplied to the apparatus 100, as in the calibration of the test length of the apparatus 100. Then, transmitted pulses for the ultrasonic waves are generated by the microcomputer 126 to the driver 128 so that the pulse voltage is supplied to the ultrasonic transducer 118 through the transmission-reception switch 124. Thus, the ultrasonic waves, corresponding to the transmitted pulses from the microcomputer 126, are generated by the ultrasonic transducer 118. Right after that, the ultrasonic transducer 118 operates at the reception mode by transmission-reception switch 124 to generate the electric signal, corresponding to the received ultrasonic waves, to the microcomputer 126 through the transmission-reception switch 124 and the receiver 130. The microcomputer 126 calculates the propagation time $t_S(sec)$ on the basis of the time when the transmitted pulses are generated to the driver 128 and the time when the electric signal is received from the ultrasonic transducer 118. Then, the ultrasonic propagation velocity $C_S$(m/sec) through the sample gas is obtained by flowing equation (7).

$$C_S = 2L_S/t_S \qquad (7)$$

The concentration of oxygen $P_S$ is obtained by following equation (8) on the basis of equation (3).

$$P_S = (\kappa R T_S/C_S^2 - M_{N2})/(M_{O2} - M_{N2}) \qquad (8)$$

Further, the concentration of oxygen in the sample gas can be obtained as a ratio of the ultrasonic propagation velocity in the sample gas and the ultrasonic propagation velocities in 100% of oxygen gas and 100% of nitrogen gas. That is, the ultrasonic propagation velocity $C_{O2}$(m/sec) at temperature $T_S$(K) through 100% of oxygen gas and the ultrasonic propagation velocity $C_{N2}$(m/sec) at temperature $T_S$(K) through 100% of nitrogen gas can be easily obtained by using equation (1). Thus, $P_S$ can be calculated by following equation (9) with the ultrasonic propagation velocity $C_S$(m/sec) through the sample gas.

$$P_S = (1/C_S^2 - 1/C_{N2}^2)/(1/C_{O2}^2 - 1/C_{N2}^2) \qquad (9)$$

Such calculations are conducted by the microcomputer 126, and the results are indicated by the display unit 134.

Next, the explanation will be directed to an example in which the linear expansion coefficient $\alpha$(1/K) of the conduit 102 is unknown. In such a case, the linear expansion coefficient $\alpha$(1/K) can be easily obtained by using the apparatus 100.

A calibration gas is supplied to the apparatus 100 at a first temperature $T_1$(K) set by the temperature regulator 113. The test length $L_1$(m) between the ultrasonic transmission-reception device 118 and the reflector 122 is measured by the above-described method for calibrating the reference length. Then, the calibration gas is supplied at temperature $T_2$(K) ($T_2 \neq T_1$) to measure the test length $L_2$(m). In this case, the larger the temperature difference between $T_1$ and $T_2$, the better the accuracy of the linear expansion coefficient $\alpha$(1/K) obtained. For example, the measurement can be preferably conducted at temperatures adjacent the minimum and maximum values of the temperature range for use of the apparatus.

When $T_1$, $L_1$, $T_2$, $L_2$ are obtained, the linear expansion coefficient $\alpha$(1/K) of the material forming the conduit 102 is obtained by following equation (10).

$$\alpha = (L_1 - L_2)/L_1(T_1 - T_2) \qquad (10)$$

The above calculation is conducted by the microcomputer 126 and the linear expansion coefficient $\alpha$(1/K) thus obtained is stored in the memory 132.

According to the above-described method, the linear expansion coefficient $\alpha$ of the material of the conduit 102 can be accurately obtained by supplying single calibration gas to the apparatus 100 at two different temperatures. This method can be carried out by a simple measurement and calculation. Therefore, if the linear expansion coefficient of the material of the conduit 102 is changed due to the secular change in the material of the conduit 102, the linear expansion coefficient can be easily measured again to renew the linear expansion coefficient stored in the memory 132.

In the above description, an example has been explained in which the temperature of the calibration gas supplied to the conduit 102 is regulated by the temperature regulator 113, which provides means for changing the temperature of the apparatus 100, in particular the conduit 102. This configuration is shown as an example of means for changing the temperature of the apparatus, in particular the conduit 102 by the changes in the temperature of the calibration gas with a premise that there is a correlation between the temperature of the calibration gas flowing through the conduit 102 and that of the conduit 102. However, the present invention is not limited to this configuration, and the apparatus 100 may be disposed in a thermostatic chamber in the production process of the apparatus 100 so that whole of the apparatus and the temperature of the gas supplied to the apparatus 100 set to a predetermined temperature, and the linear expansion coefficient $\alpha$ is obtained under such a condition.

Figure 2:
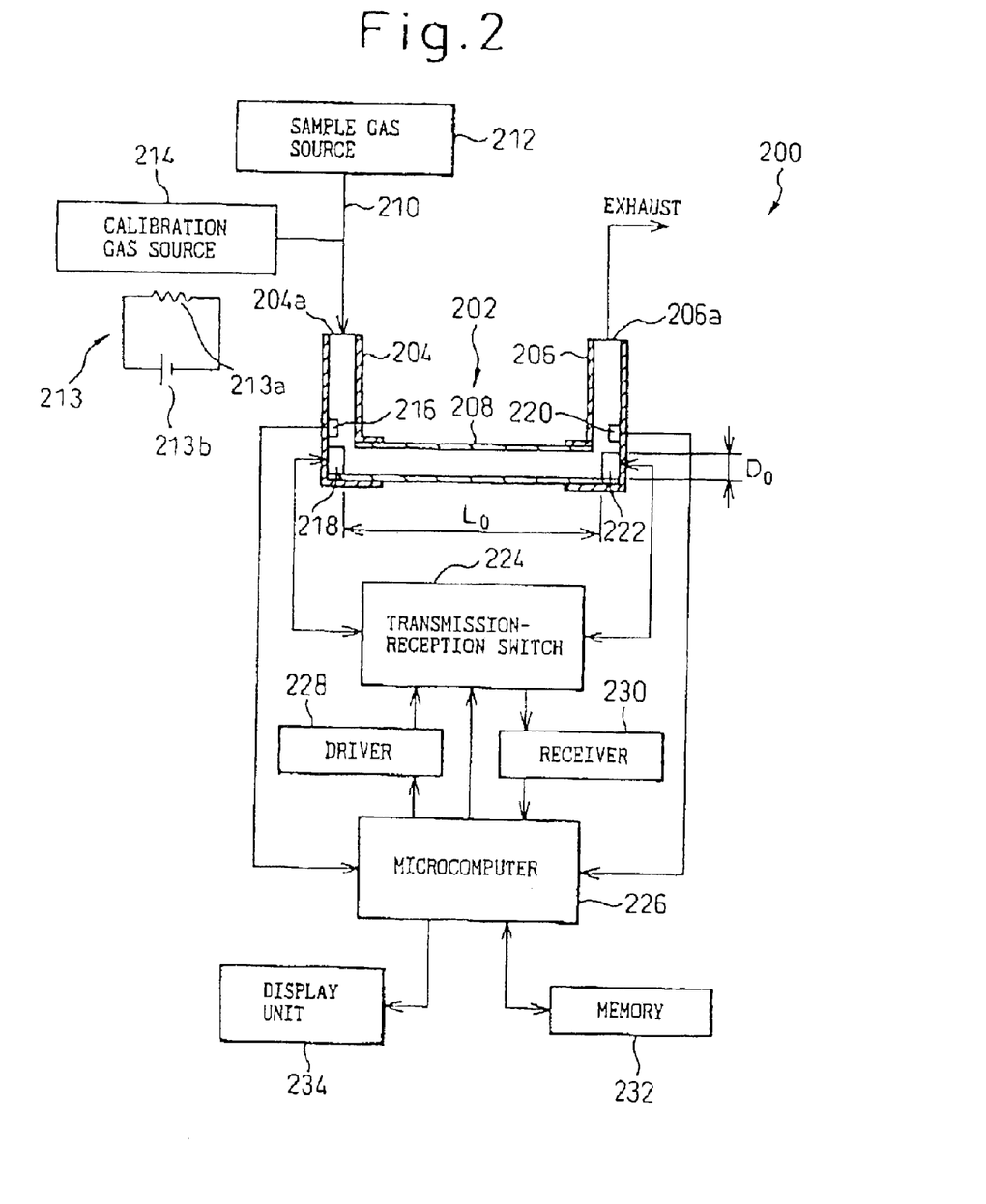
FIG. 2 is a schematic diagram of an apparatus according to a second embodiment of the invention.

Next, with reference to FIG. 2, a second embodiment of the present invention will be described below. The second embodiment has substantially the same configuration of the first embodiment, except for that the reflector in the first embodiment is replaced with a second ultrasonic transducer, which provides a ultrasonic transmission-reception device, disposed to face a first ultrasonic transducer 218, which provides a first ultrasonic transmission-reception device.

A ultrasonic gas concentration and flow rate measuring apparatus 200 according to the second embodiment includes a conduit 202 for flowing a sample gas or a calibration gas. The conduit 202 has a straight portion 208 and perpendicular portions 204 and 206 connected to the ends of the straight portion. The straight portion 208 comprises a conduit member having a circular section, the diameter of which does not changes along the longitudinal axis. A first ultrasonic transducer 218, providing a first ultrasonic transmission-reception device, is fixedly provided at an end of the inside of the straight portion, and a second ultrasonic transducer 222, providing a second ultrasonic transmission-reception device, is fixedly mounted to the other end of the inside of the straight portion to face the first ultrasonic transducer 218. In this embodiment, the distance between the first and second ultrasonic transducers 218 and 222 is defined as a test length.

A transmission-reception switch 224 is connected to the first and second ultrasonic transducers 218 and 222. The transmission-reception switch 224 switches the operation mode of the first and second ultrasonic transducers 218 and 222 independently between a transmission mode in which the first and second ultrasonic transducers 218 and 222 transmit ultrasonic waves and a reception mode in which the first and second ultrasonic transducers 218 and 222 receive the ultrasonic waves. The transmission-reception switch 224 is connected to a microcomputer 226 so that the switching operation of transmission-reception switch 224 is controlled by the microcomputer 226.

The perpendicular portion 204, disposed at the upstream side relative to the flow direction of the gas through the conduit 202, has an inlet port 204a. A sample gas source 212 and a calibration gas source 214 are connected to the inlet port 204a through a supply conduit 210. The sample gas source 212 includes a vessel (not shown) for containing a sample gas or a mixture including a gas, the concentration of which is to be measure, a pressure reducing valve (not shown) provided between the vessel and the supply conduit 210 and a flow regulating valve (not shown) for regulating the flow rate of the calibration gas from the calibration gas source 214.

The calibration gas source 214 may include a vessel (not shown) for containing a calibration gas, the component and the component ratio of which are known, and a pressure reducing valve (not shown) provided between the vessel and the supply conduit 210. The calibration gas source 214 may also include a temperature regulator 213, which provides means for changing the temperature of the device 200, in particular the conduit 202. In the example shown in FIG. 2, the temperature regulator 213 includes a heating wire 213a and an electric power source 213b for supplying the electric power to the heating wire 213a.

The perpendicular portion 206, disposed at the downstream side relative to the flow direction of the gas through the conduit 202, has an outlet port 206a. The sample gas or the calibration gas used for the concentration measurement or the calibration is exhausted through the outlet port 206a. A gas processing apparatus (not shown) may advantageously be disposed downstream of the outlet port 206 in case that the exhausted gas is not suitable to directly exhaust to the atmosphere.

Temperature sensors 216 and 220, for measuring the temperature of the sample gas or the calibration gas flowing through the conduit 202, are disposed preferably in the perpendicular portions 204 and 206 so that they do not disturb the flow in the straight portion 208. The temperature sensors 216 and 220 are connected to the microcomputer 226. In this connection, if the changes in the temperature of the sample gas is small, only one of the temperature sensors 216 or 220 may be disposed.

A driver 228 for driving the first ultrasonic transducer 218, a receiver 230 for A/D conversion of the signals from the first ultrasonic transducer 218, a display unit 234 for indicating, for example, the operating condition of the device 200 and the measurement results and memory 233 including a nonvolatile memory device or a disc device for storing the operation system for the microcomputer 226 and various parameters are connected to the microcomputer 226.

The operation of the second embodiment will be described below.

First, prior to the initiation of the normal measuring process for measuring the concentration of a certain gas contained in the sample gas, the test length between the first and second ultrasonic transducers 218 and 222 and the inner diameter D of the straight portion 208 of the conduit 202 to obtain the reference length $L_0$ and the reference diameter $D_0$.

In the present embodiment, the calibration gas, identical to that in the first embodiment, is supplied to the conduit 202 from the calibration gas source 214 at a predetermined rate $Q_0$ by the flow regulating valve. At that time, the temperatures of the calibration gas are measured by the two temperature sensors 216 and 220 and the mean value thereof is stored in the memory 232 as a reference temperature $T_0(K)$.

During the supply of the calibration gas, pulses for generating the ultrasonic waves are transmitted to the driver 228 from the microcomputer 226. A pulse voltage is supplied to the first ultrasonic transducer 218 from the driver 228 through the transmission-reception switch 224. The first ultrasonic transducer 218 generates ultrasonic waves corresponding to the pulse voltage. The ultrasonic waves generated by the first ultrasonic transducer 218 propagate through the sample gas flowing through the straight portion 208 of the conduit 202 and are received by the second ultrasonic transducer 222. The second ultrasonic transducer 222 generates an electric signal corresponding to the received ultrasonic waves to the microcomputer 226 through the transmission-reception switch 224 and the receiver 230. The microcomputer 226 calculates the forward propagation time $t_1(sec)$ on the basis of the time when the transmitted pulses are generated to the driver 228 and the time when the electric signal is received from the second ultrasonic transducer 222.

The transmission-reception switch 224 switches the operation mode of the first ultrasonic transducer 218 from the transmission mode to the reception mode right after the electric signal from the second ultrasonic transducer 222 is received and also switches the operation mode of the second ultrasonic transducer 222 from the reception mode to the transmission mode. Thereafter, pulses for generating the ultrasonic waves are transmitted to the driver 228 from the microcomputer 226. A pulse voltage is supplied to the second ultrasonic transducer 222 from the driver 228 through the transmission-reception switch 224. The second ultrasonic transducer 222 generates ultrasonic waves corresponding to the pulse voltage. The ultrasonic waves are received by the first ultrasonic transducer 218. The first ultrasonic transducer 218 generates an electric signal corresponding to the received ultrasonic waves to the microcomputer 226 through the transmission-reception switch 224 and the receiver 230. The microcomputer 226 calculates the backward propagation time $t_2(sec)$ on the basis of the time when the transmitted pulses are generated to the driver 228 and the time when the electric signal is received from the first ultrasonic transducer 218.

By obtaining the mean value of $t_1$ and $t_2$, the affection of the flow of the calibration gas in the conduit 202 can be removed. The ultrasonic propagation time $t_0$ is defined by following equation (11).

$$t_0 = (t_1 + t_2)/2 \qquad (11)$$

In this connection, the ultrasonic propagation velocity $C_0(m/sec)$ through the calibration gas at a temperature $T_0(K)$ is calculated by the above-described equation (3).

On the other hand, the relation $$C_0 = L_0/t_0 \qquad (12)$$

gives the following equation.

$$L_0 = ((\kappa R T_0)/(M_{O2}P + M_{N2}(1-P)))^{1/2} \times t_0 \qquad (13)$$

These calculations are conducted by the microcomputer 226. The test length $L_0(m)$ thus calculated at the reference temperature $T_0$ is stored in the memory 232 as the reference length.

Further, by using this reference length $L_0$, the forward propagation velocity $V_{01}(m/sec)$ and the backward propagation velocity $V_{02}(m/sec)$, relative to the flow direction of the calibration gas, are represented by $V_{01} = L_0/t_1$ and $V_{02} = L_0/t_2$. Therefore, the flow velocity $V_0(m/sec)$ of the calibration gas in the conduit 202 is obtained by following equation (14), on the basis of above-described equation (2).

$$V_0 = (V_{01} - V_{02})/2 \qquad (14)$$

Multiplication of the flow velocity V by the sectional area $(m^2)$ of the straight portion 208, perpendicular to the axis of the straight portion 208 of the conduit 202, gives a conversion of the flow velocity (m/sec) to the flow rate $(m^3/sec)$. Thus, the reference diameter $D_0(m)$ at the reference temperature $T_0(K)$ of the straight portion 208 gives the following equation.

$$V_0 \pi (D_0/2)^2 = Q_0 \qquad (15)$$

Therefore, the reference diameter $D_0(m)$ at the reference temperature $T_0(K)$ can be obtained by following equation (16).

$$D_0 = 2(Q_0/(\pi V_0))^{1/2} \qquad (16)$$

The above calculation is conducted by the microcomputer 226, and the reference diameter $D_0(m)$ thus obtained is stored in the memory 232.

According to the above method, the reference length $L_0(m)$ between the first and second ultrasonic transducers 218 and 222 is calibrated at a temperature $T_0(K)$ by supplying a calibration gas, the component and the concentration of which is known, to the apparatus 200, and measuring the propagation times t1 and t2, in the forward and backward direction relative to the flow of the calibration gas, from the first and second ultrasonic transducers 218 and 222. Additionally, by supplying the calibration gas to the apparatus 200 at a predetermined rate, the reference diameter $D_0(m)$ can also calibrated at the same time.

Next, the explanation will be directed to a method for measuring the flow rate and oxygen concentration of a sample gas including oxygen and nitrogen, the ratio of which is unknown.

First, the explanation will be directed to an example in which the linear expansion coefficient $\alpha(1/K)$ of the conduit 202 is known.

The test length $L_S(m)$ at a temperature $T_S(K)$ can be obtained on the basis of equation (6) with the reference length $L_0(m)$ and the reference temperature $T_0(K)$ read from the memory 232. The measured temperature $T_S(K)$ can be the mean value of temperatures sensed by the temperature sensors 216 and 220.

The first ultrasonic transducer 218 is set to the transmission mode by the transmission-reception switch 224 when a sample gas is supplied, as in the calibration of the test length of the apparatus 200. Then, transmitted pulses for the ultrasonic waves are generated by the microcomputer 226 to the driver 228 so that the pulse voltage is supplied to the first ultrasonic transducer 218 through the transmission-reception switch 224. Thus, the ultrasonic waves, corresponding to the transmitted pulses from the microcomputer 226, are generated by the first ultrasonic transducer 218, and received by the second ultrasonic transducer 222. The second ultrasonic transducer 222 generates the electric signal, corresponding to the received ultrasonic waves, to the microcomputer 226 through the transmission-reception switch 224 and the receiver 230. The microcomputer 226 calculates the propagation time $t_{S1}$(sec), in the forward direction, on the basis of the time when the transmitted pulses are generated to the driver 228 and the time when the electric signal is received from the second ultrasonic transducer 218.

After the measurement of the propagation time $t_{S1}$(sec) in the forward direction, the transmission-reception switch 224 switches the operation mode of the first ultrasonic transducer 218 from the transmission mode to the reception mode, and the operation mode of the second ultrasonic transducer 222 from the reception mode to the transmission mode. Under this condition, ultrasonic waves are transmitted in the backward direction relative to the flow of the sample gas to obtain the propagation time $t_{S2}$(sec) in the backward direction by a process identical to that for obtaining the propagation time $t_{S1}$ in the forward direction. On the basis of the propagation times $t_{S1}$ and $t_{S2}$, in the forward and backward directions, a propagation time $t_{S0}$ which does not include the affection of the flow is obtained by $t_{S0}=(t_{S1}+t_{S2})/2$(sec) Further, on the basis of this results, the ultrasonic propagation velocity $C_S$(m/sec) through the sample gas is obtained by following equation (17).

$$C_S=L_S/t_{S0} \tag{17}$$

The concentration of the oxygen gas $P_S$ is obtained by above-described equation (8).

Further, the concentration of oxygen in the sample can also be obtained as a ratio of the ultrasonic propagation velocity in the sample gas and the ultrasonic propagation velocities in 100% of oxygen gas and 100% of nitrogen gas, as in the first embodiment, i.e., on the basis of equation (9) with the ultrasonic propagation velocity $C_{O2}$(m/sec), at temperature $T_S(K)$, through 100% of oxygen gas and the ultrasonic propagation velocity $C_{N2}$(m/sec), at temperature $T_S(K)$, through 100% of nitrogen gas.

Such calculations are conducted by the microcomputer 226, and the results are indicated by the display unit 234.

Next, a method of measuring the flow rate will be described.

In order to measuring the flow rate, the ultrasonic propagation velocity $V_{S1}$(m/sec), in the forward direction relative to the sample gas, and ultrasonic propagation velocity $V_{S2}$ (m/sec), in the backward direction, are obtained on the basis of following equations (18) (19) with above-described $L_S$ and the propagation times $t_{S1}$ and $t_{S2}$, in the forward and backward directions.

$$V_{S1}=L_S/t_{S1} \tag{18}$$

$$V_{S2}=L_S/t_{S2} \tag{19}$$

On the basis of equations (18) (19) and above-described equation (13), the flow velocity $V_S$(m/sec) of the sample gas is represented by following equation (20).

$$V_S=(V_{o1}-V_{o2})/2 \tag{20}$$

In order to convert the flow velocity $V_S$(m/sec) to the flow rate $Q_S$(m$^3$/sec), the sectional area (m$^2$) of the straight portion 208 must be previously obtained. The sectional area $S_S$(m$^2$) of the straight portion 208 is obtained by following equation (21) with the reference diameter $D_0$(m) and the reference temperature $T_0$(K) read from the memory 232, and the linear expansion coefficient $\alpha(1/K)$ of the material forming the conduit 202.

$$S_S=\pi((D_0(1+\alpha(T_S-T_0))/2)^2 \tag{21}$$

The temperature $T_S(K)$ is the same as the temperature $T_S$ at the time of measurement. Thus, the flow rate $Q_S$(m$^3$/sec) of the sample gas is calculated by following equation (22).

$$Q_S=V_S S_S \tag{22}$$

The above calculations are conducted by the microcomputer 226 and the display unit 234 indicates the results thereof.

Next, the explanation will be directed to an example in which the linear expansion coefficient $\alpha(1/K)$ of the conduit 202 is unknown. In such a case, the linear expansion coefficient $\alpha(1/K)$ can be easily obtained by using the apparatus 200.

A calibration gas is supplied to the apparatus 200 at a first temperature $T_1(K)$ set by the temperature regulator 213. The test length $L_1(m)$ between the first and second ultrasonic transmission-reception devices 218 and 222 is measured by the above-described method for calibrating the reference length, as in the first embodiment. Then, the calibration gas is supplied at temperature $T_2(K)$ ($T_2 \neq T_1$) to measure the test length $L_2(m)$, in the same manner. In this case, the larger the temperature difference between $T_1$ and $T_2$, the better the accuracy of the linear expansion coefficient $\alpha(1/K)$ obtained.

When $T_1$, $L_1$, $T_2$, $L_2$ are obtained, the linear expansion coefficient $\alpha(1/K)$ of the material forming the conduit 202 is obtained by above-described equation (10).

The above calculation is conducted by the microcomputer 226 and the linear expansion coefficient $\alpha(1/K)$ thus obtained is stored in the memory 232.

According to the above-described method, the linear expansion coefficient α of the material of the conduit 202 can be accurately obtained by supplying single calibration gas to the apparatus 200 at two different temperatures.

In the above description, an example has been explained in which the temperature of the calibration gas supplied to the conduit 202 is regulated by the temperature regulator 213, which provides means for changing the temperature of the apparatus 200, in particular the conduit 202. This configuration is shown as an example of means for changing the temperature of the apparatus, in particular the conduit 202 by the changes in the temperature of the calibration gas with a premise that there is a correlation between the temperature of the calibration gas flowing through the conduit 202 and that of the conduit 202. However, the present invention is not limited to this configuration, and the apparatus 200 may be disposed in a thermostatic chamber in the production process of the apparatus 200 so that whole of the apparatus and the temperature of the gas supplied to the apparatus 200 set to a predetermined temperature, and the linear expansion coefficient α is obtained under such a condition.

As described above, the present invention allows the apparatus to be carried by the apparatus itself with a single calibration gas without a special calibration device.

Further, according to the present invention, the apparatus can be recalibrated in case of secular change of the apparatus. Further, the present invention provides accurate measurement of concentration and flow rate of a sample gas independently of the temperature of the sample gas.

What is claimed is:

1. A ultrasonic apparatus for measuring a gas flow rate, comprising:
   a conduit, extending along an axis, for flowing an objective gas, the flow rate of which is to be measured;
   a first ultrasonic transmission-reception device mounted to the inside of the conduit;
   a second ultrasonic transmission-reception device mounted to the inside of the conduit to face the first ultrasonic transmission-reception device;
   a transmission-reception switch for switching the operation mode of the first and second ultrasonic transmission-reception devices between a transmission mode for transmitting ultrasonic waves and a reception mode for receiving ultrasonic waves;
   a calibration gas source for supplying a calibration gas, the component, the component ratio and the flow rate of which are known, to the conduit;
   a temperature sensor, disposed in the conduit, for measuring the temperature of the calibration gas flowing through the conduit;
   propagation time calculation means for calculating a first propagation time period where ultrasonic waves propagate through the calibration gas in the conduit on the basis of the time when the first ultrasonic transmission-reception device transmits a first set of ultrasonic waves and the time when the second ultrasonic transmission-reception device receives the first set of ultrasonic waves, and a second propagation time period where a second set of ultrasonic waves propagates through the calibration gas in the conduit on the basis of the time when the second ultrasonic transmission-reception device transmits the second set of ultrasonic waves and the time when the first ultrasonic transmission-reception device receives the second set of ultrasonic waves; and
   calibration means for calibrating a reference length between the first and second ultrasonic transmission-reception devices and the inner diameter of the conduit, on the basis of the calculation results by the propagation time calculation means,
   wherein after substituting the objective gas for the calibration gas in the ultrasonic apparatus, the propagation time calculation means operates to determine a velocity of the objective gas and the gas flow rate of the objective gas is determined by multiplying the velocity of the objective gas with a sectional area of the conduit based upon the inner diameter of the conduit calibrated by the calibration means.

2. A ultrasonic apparatus for measuring
   a gas flow rate according to claim 1 further comprising linear expansion coefficient storing means for storing the linear expansion coefficient of the material forming the conduit; and
   correction means for correcting and calculating the calibrated reference length on the basis of the linear expansion coefficient and the temperature, measured by the temperature sensor, of the objective gas flowing through the conduit.

3. A ultrasonic apparatus for measuring a gas flow rate according to claim 1, further comprising temperature regulating means for regulating the temperature of the conduit;
   linear expansion coefficient calculating means for calculating the linear expansion coefficient of the material forming the conduit on the basis of the changes in the reference length when the temperature of the conduit is changed; and
   correction means for correcting and calculating the calibrated reference length on the basis of the linear expansion coefficient and the temperature, measured by the temperature sensor, of the objective gas flowing through the conduit.

4. A method of measuring the flow rate of an objective gas by a ultrasonic gas flow rate measuring apparatus which comprises, a conduit, extending along an axis, for flowing an objective gas, the flow rate of which is to be measured, a first ultrasonic transmission-reception device mounted to the inside of the conduit, a second ultrasonic transmission-reception device mounted to the inside of the conduit to face the first ultrasonic transmission-reception device, and a transmission reception switch for switching the operation mode of the first and second ultrasonic transmission-reception devices between a transmission mode for transmitting ultrasonic waves and a reception mode for receiving ultrasonic waves; the method comprising, prior to the start of the process for measuring the flow rate of the gas to be measured, the steps of:
   supplying a calibration gas, the component and the component ratio of which are known, to the conduit;
   measuring the temperature of the calibration gas flowing through the conduit by a temperature sensor disposed in the conduit;
   generating a first set of ultrasonic waves by the first ultrasonic transmission-reception device and receiving the first set of ultrasonic waves by the second ultrasonic transmission-reception device;
   switching the operation mode of the first transmission-reception device from the transmission mode to the reception mode and the operation mode of the second transmission-reception device from the reception mode to the transmission mode;
   calculating a first propagation time period where the first set of ultrasonic waves propagates through the calibration gas in the conduit on the basis of the time when the first ultrasonic transmission-reception device transmits the first set of ultrasonic waves and the time when the second ultrasonic transmission-reception device receives the first set of ultrasonic waves, and a second propagation time period where a second set of ultrasonic waves propagates through the calibration gas in the conduit on the basis of the time when the second ultrasonic transmission-reception device transmits the second set of ultrasonic waves and the time when the first ultrasonic transmission-reception device receives the second set of ultrasonic waves;

calibrating a reference length between the first and second ultrasonic transmission-reception devices and the inner diameter of the conduit, on the basis of the calculation results;

substituting the objective gas for the calibration gas in the ultrasonic apparatus;

determining a velocity of the objective gas by calculating a third propagation time period where a third first set of ultrasonic waves propagates through the objective gas in the conduit on the basis of the time when the first ultrasonic transmission-reception device transmits the third set of ultrasonic waves and the time when the second ultrasonic transmission-reception device receives the third set of ultrasonic waves, and a fourth propagation time period where a fourth set of the ultrasonic waves propagates through the objective gas in the conduit on the basis of the time when the second ultrasonic transmission-reception device transmits the fourth set of ultrasonic waves and the time when the first ultrasonic transmission-reception device receives the fourth set of ultrasonic waves; and determining the gas flow rate of the objective gas by multiplying the velocity of the objective gas with a sectional area of the conduit based upon the calibrated inner diameter of the conduit.

5. A method according to claim 4 wherein the ultrasonic gas flow rate measuring apparatus further comprising: linear expansion coefficient storing means for storing the linear expansion coefficient of the material forming the conduit; and the method further comprising a steps of measuring the temperature of the objective gas flowed through the conduit; and correcting and calculating the calibrated reference length and the inner diameter of the conduit, on the basis of the linear expansion coefficient and the temperature, measured by the temperature sensor, of the objective gas flowing through the conduit.

6. A method according to claim 4, further comprising the steps of calculating the linear expansion coefficient of the material forming the conduit on the basis of the changes in the reference length when the temperature of the conduit is changed;

measuring the temperature of the objective gas flowed through the conduit; and correcting and calculating the calibrated reference length and the inner diameter of the conduit on the basis of the linear expansion coefficient and the measured temperature of the objective gas.

7. A ultrasonic apparatus for measuring a gas flow rate according to claim 1, wherein the first and second ultrasonic transmission-reception devices being disposed so that respective centers of the first and second ultrasonic transmission-reception devices align with the axis of the conduit.

8. A method according to claim 4 wherein the ultrasonic gas flow rate measuring apparatus wherein the first and second ultrasonic transmission-reception devices being disposed so that respective centers of the first and second ultrasonic transmission-reception devices align with the axis of the conduit.

* * * * *